US011534256B2

(12) United States Patent  
Asamarai

(10) Patent No.: US 11,534,256 B2  
(45) Date of Patent: Dec. 27, 2022

(54) DENTAL AEROSOL PROTECTION SYSTEM

(71) Applicant: Mujahid A. Asamarai, Wayne, NJ (US)

(72) Inventor: Mujahid A. Asamarai, Wayne, NJ (US)

(*) Notice: Subject to any disclaimer, the term of this patent is extended or adjusted under 35 U.S.C. 154(b) by 281 days.

(21) Appl. No.: 17/011,793

(22) Filed: Sep. 3, 2020

(65) Prior Publication Data

US 2022/0061950 A1 Mar. 3, 2022

(51) Int. Cl.
*A61B 90/00* (2016.01)
*A61B 90/57* (2016.01)

(52) U.S. Cl.
CPC .............. *A61B 90/05* (2016.02); *A61B 90/57* (2016.02); *A61B 2090/571* (2016.02)

(58) Field of Classification Search
CPC .... A61B 90/05; A61B 90/57; A61B 2090/571
See application file for complete search history.

(56) References Cited

U.S. PATENT DOCUMENTS

| | | | |
|---|---|---|---|
| 3,012,322 A | 12/1961 | Thompson |
| 3,537,447 A | 11/1970 | Gauthier et al. |
| 4,082,092 A | 4/1978 | Foster |
| 4,446,861 A | 5/1984 | Tada |
| 4,936,318 A | 6/1990 | Schoolman |
| 4,967,320 A | 10/1990 | Paschal |
| 5,127,411 A | 7/1992 | Schoolman et al. |
| 5,360,018 A | 11/1994 | Chen |
| 5,513,632 A | 5/1996 | Nepon et al. |
| 5,547,375 A | 8/1996 | Schneider |
| 5,865,182 A | 2/1999 | Chen |
| 6,308,707 B1 | 10/2001 | Lu |
| 6,464,499 B1 | 10/2002 | Lu |
| 11,219,500 B2 * | 1/2022 | Ryan ...................... A61B 90/05 |

(Continued)

FOREIGN PATENT DOCUMENTS

| | | |
|---|---|---|
| CN | 103126848 A | 6/2013 |
| JP | 3600224 B2 | 12/2004 |

OTHER PUBLICATIONS 3M unveils 24-minute in-house sterilization monitoring system; Dental Products Report; https://www.dentalproductsreport.com/view/3m-unveils-24-minute-in-house-sterilization-monitoring-system; Jul. 7, 2020, 2 pages.

*Primary Examiner* — Anita M King
(74) *Attorney, Agent, or Firm* — Skaar Ulbrich Macari, P.A.

(57) ABSTRACT

A dental aerosol protection system includes an aerosol collection funnel and one or more protective transparent shields. A proximal attachment end of the aerosol collection funnel can be configured to fit into a fitting of a high-vacuum evacuator (HVE) conduit. A distal end thereof defines an opening having a cross-sectional area that is greater than a diameter of the proximal attachment end to collect aerosols emanating from the patient's mouth. The aerosol collection funnel is positionable with respect to a mouth of a patient via an adjustable arm operably coupled to the aerosol collection funnel or the fitting of the HVE conduit. The shield or shields can be positioned with respect to the mouth of the patient via a boom coupled to an aperture defined through the shield. The boom can be coupled to the shield(s) via a flexible shield support member.

20 Claims, 14 Drawing Sheets

(56) References Cited

U.S. PATENT DOCUMENTS

| | | |
|---|---|---|
| 2004/0069306 A1 | 4/2004 | Moenning et al. |
| 2008/0166684 A1 | 7/2008 | Kanas |
| 2011/0318702 A1 | 12/2011 | Lockwood |
| 2019/0365214 A1 | 12/2019 | Lloro Boada et al. |
| 2021/0353468 A1* | 11/2021 | Orrington, II ......... A61G 15/14 |
| 2021/0369383 A1* | 12/2021 | Pawlowicz ............ A61B 90/05 |
| 2021/0378802 A1* | 12/2021 | Jeanmenne ............ A61C 17/10 |

* cited by examiner

DENTAL AEROSOL PROTECTION SYSTEM

FIELD

The present invention relates generally to dentistry, and more particularly, to a system and method of protecting persons from aerosols produced during dental procedures.

BACKGROUND

In dentistry, the necessary equipment, including dental drills and cavitrons/ultrasonics produce a great degree of aerosol from the patient's mouth into the surrounding area. These aerosols ae typically small liquid droplets which have been propelled from the patient's saliva into the air surrounding the patient working field. These droplets thus may take hours to fully settle. Persons performing the dental procedure on the patient are exposed to these droplets, which may carry viruses or bacteria, and therefore pose an infection risk. For this reason, among others, dentistry has been classified as high risk for the transmission of viral and bacterial infections from patient to practitioner. These concerns are heightened due to the COVID-19 pandemic and the nature of COVID-19 transmission through aerosolized liquid droplets.

Previous attempts to mitigate the aerosols fall into three distinct categories: (1) vacuum suction only, (2) transparent shielding only, and (3) combined vacuum suction with transparent shielding. Categories 1 and 2 are inadequate to remedy the aerosol problem. Previous systems according to category 3 also suffer from certain drawbacks.

One category 3 system, SheildVAC and Vacuum Barrier (PN:4936318), involve disposing a suction apparatus in the center of a transparent shield. However, this configuration reduces the effectiveness of vacuum suction as the source of suction is moved too distant from the patient's mouth for good suction effect because there must be sufficient clearance between the shield and the patient's mouth to accommodate the practitioner's hands. This system and others like it may also exacerbate aerosol dispersal with suction being between 6-10 inches above the patient's mouth as the suction creates an upward current away from the patient's mouth and towards the shield/practitioner but which may not be fully contained at that distance.

Another category 3 system, Safe-T-Shield, requires the installation of a specialized and invasive and expensive vacuum and mounting system. This specialized system is mounted from the ceiling of a dental operatory where it is mechanically suspended. A powerful vacuum system must also be installed elsewhere within the clinic facility and routed through the ceiling to the patient's face. This system is expensive, requires professional installation and maintenance, and is therefore costly and inconvenient.

Thus, there remains a need to remediate aerosols generated during dental procedures in a convenient and effective manner.

SUMMARY

The present invention solves this problem and makes dentistry safer for dental assistants, hygienists, dentists, interpreters, and others who may be in the vicinity. The dental aerosol protection system strategically mitigates the dispersal of aerosol emanating from the patient's mouth and physically blocks any residual or rogue aerosol/splatter from contacting the practitioner. Less aerosol dispersal from the patient's mouth dramatically reduces the probability of viral or bacterial transmission from patient to others nearby.

The disclosure includes a dental aerosol protection system. The system can include an aerosol collection funnel and one or more protective transparent shields. A proximal attachment end of the aerosol collection funnel can be configured to fit into a fitting of a high-vacuum evacuator (HVE) conduit. A distal end thereof defines an opening having a cross-sectional area that is greater than a diameter of the proximal attachment end to collect aerosols emanating from the patient's mouth. The aerosol collection funnel is positionable with respect to a mouth of a patient via an adjustable arm operably coupled to the aerosol collection funnel or the fitting of the HVE conduit. The shield or shields can be positioned with respect to the mouth of the patient via a boom coupled to an aperture defined through the shield. The boom can be coupled to the shield(s) via a flexible shield support member.

The boom can be a self-balancing boom. The first end of the boom can be secured to a rigid structure adjacent to the patient with the opposing second end coupled to the shield.

A first end of the adjustable arm can be secured to a rigid structure adjacent to the patient or it can be secured to the boom. The opposing second end can comprise a clamp that can secure or operably couple the aerosol collection funnel or the fitting of the HVE conduit to the adjustable arm.

The aerosol collection funnel can taper from the distal collection end towards the proximal attachment end. The distal collection end of the aerosol collection funnel can define a flattened cone shape such that a horizontal dimension of an opening in the distal collection end is greater than a vertical dimension of the opening. The opening can taper inward from a top surface of the aerosol collection funnel to a bottom surface of the aerosol collection funnel.

A second shield can be provided. The second shield is positionable with respect to the mouth of the patient via the boom coupled to an aperture defined through the shield.

The boom can be coupled to the aperture defined through the shield via a flexible shield support member.

The shield can be a transparent sheet shaped as a rectangle with rounded corners. It can also be shaped to define a pair of shoulders and a neck portion between the pair of shoulders. The shield can be a planar transparent sheet.

The disclosure also includes a method of protecting dental practitioners from aerosols emanating from a patient's mouth. The method can include inserting a first end of an aerosol collection funnel into a fitting of an HVE conduit, positioning a second end of the aerosol collection funnel adjacent to the patient's mouth, securing a first transparent shield to a boom; and adjusting a position of the first transparent shield independent of the position of the aerosol collection funnel so that the first transparent shield lies between the patient's mouth and a dental practitioner while the dental practitioner is performing a dental procedure on the patient.

A second transparent shield can be secured to the boom. Additional shields can also be provided. A position of the second transparent shield can be adjusted independent of the position of the aerosol collection funnel. The second transparent shield can be positioned so that it lies between the patient's mouth and a second dental practitioner while the second dental practitioner is performing the dental procedure on the patient.

The aerosol collection funnel can be clamped to an adjustable arm. An end of the adjustable arm opposite the clamped aerosol collection funnel can be secured to either the boom or a rigid structure within a dental operatory where the dental practitioner is performing the dental procedure on the patient.

The step of securing the first transparent shield to the boom can include fastening the first transparent shield to a first end of a flexible shield support member via an aperture defined through the first transparent shield and fastening a second end of the flexible shield support member to the boom.

The boom can be secured to a rigid structure within a dental operatory where the dental practitioner is performing the dental procedure on the patient.

Other features and aspects of particular embodiments will be described in the Detailed Description portion of this application.

The above summary is not intended to limit the scope of the invention, or describe each embodiment, aspect, implementation, feature or advantage of the invention. The detailed technology and preferred embodiments for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1:
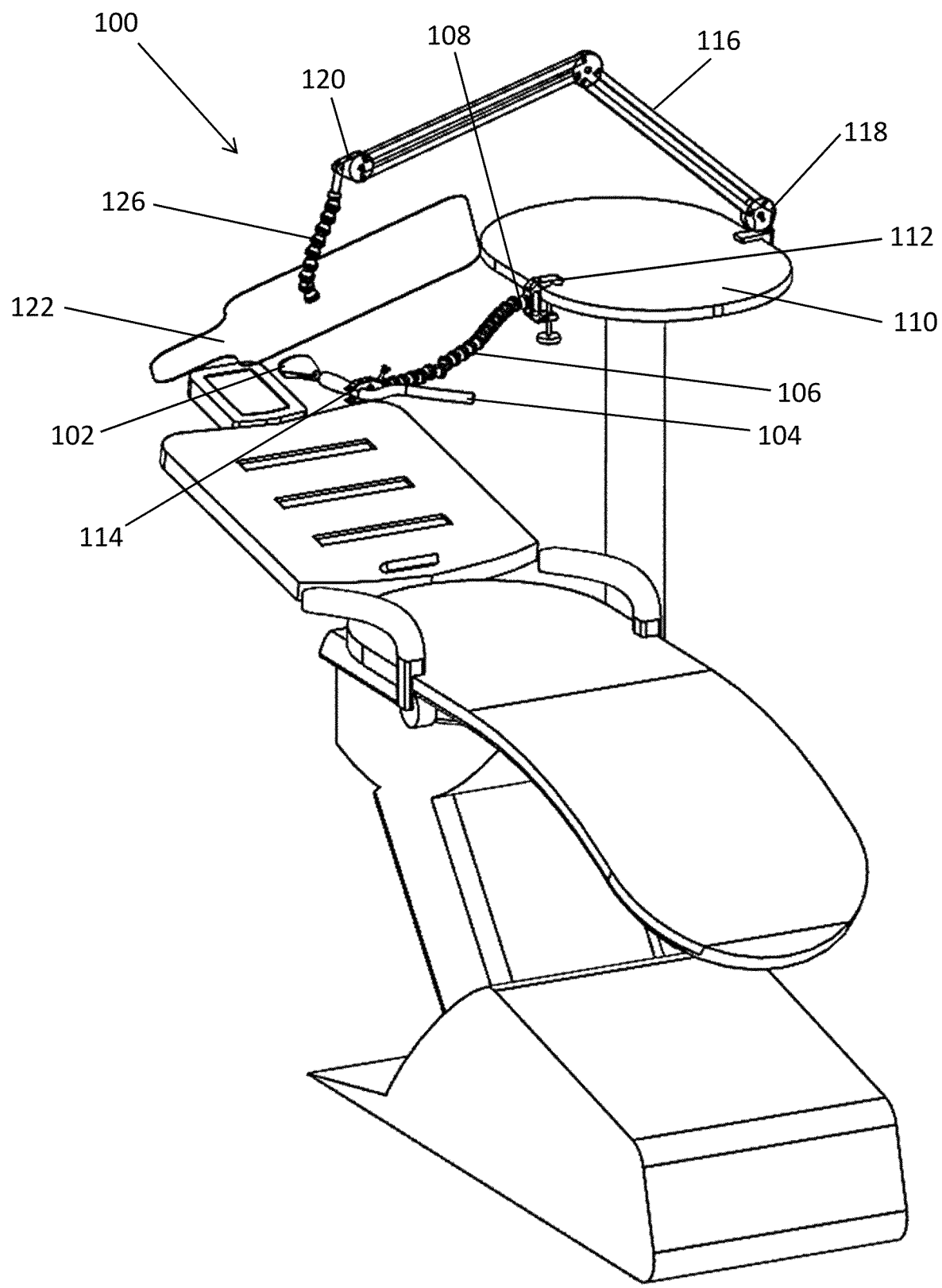
FIG. 1 is a perspective view of a dental aerosol protection system according to certain example embodiments.
Figure 2:
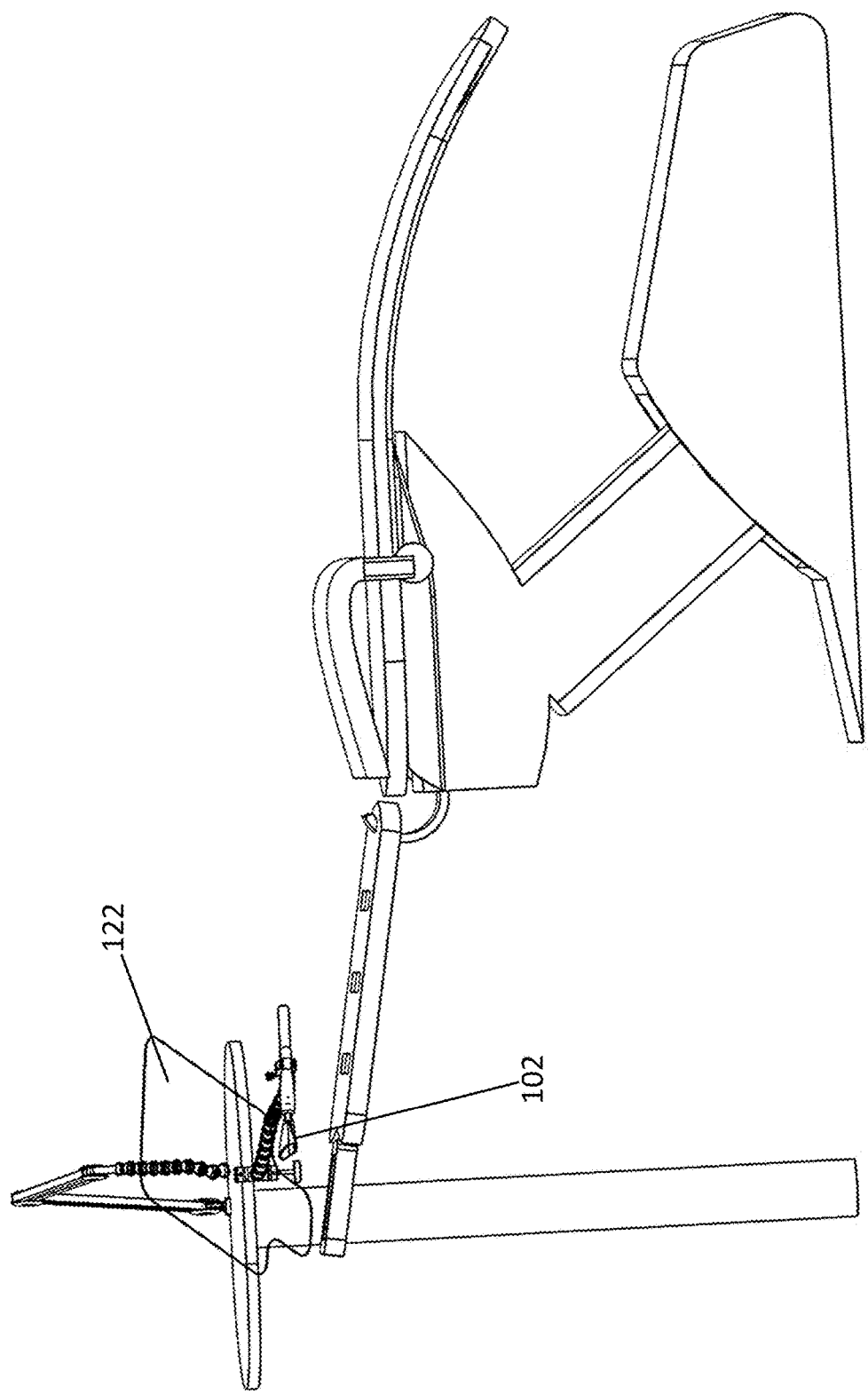
FIG. 2 is a side view of a dental aerosol protection system according to certain example embodiments.
Figure 3:
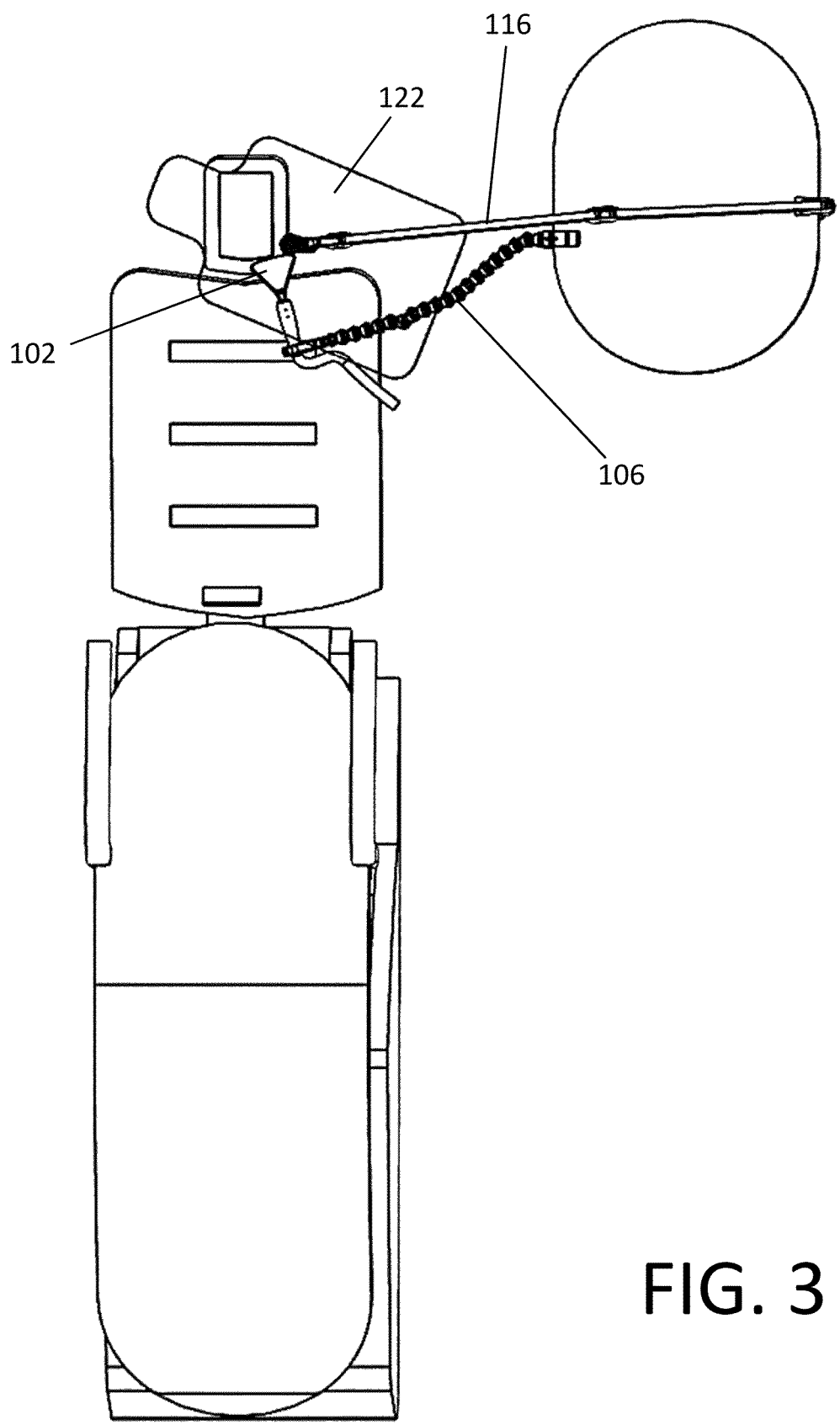
FIG. 3 is a top view of a dental aerosol protection system according to certain example embodiments.
Figure 4:
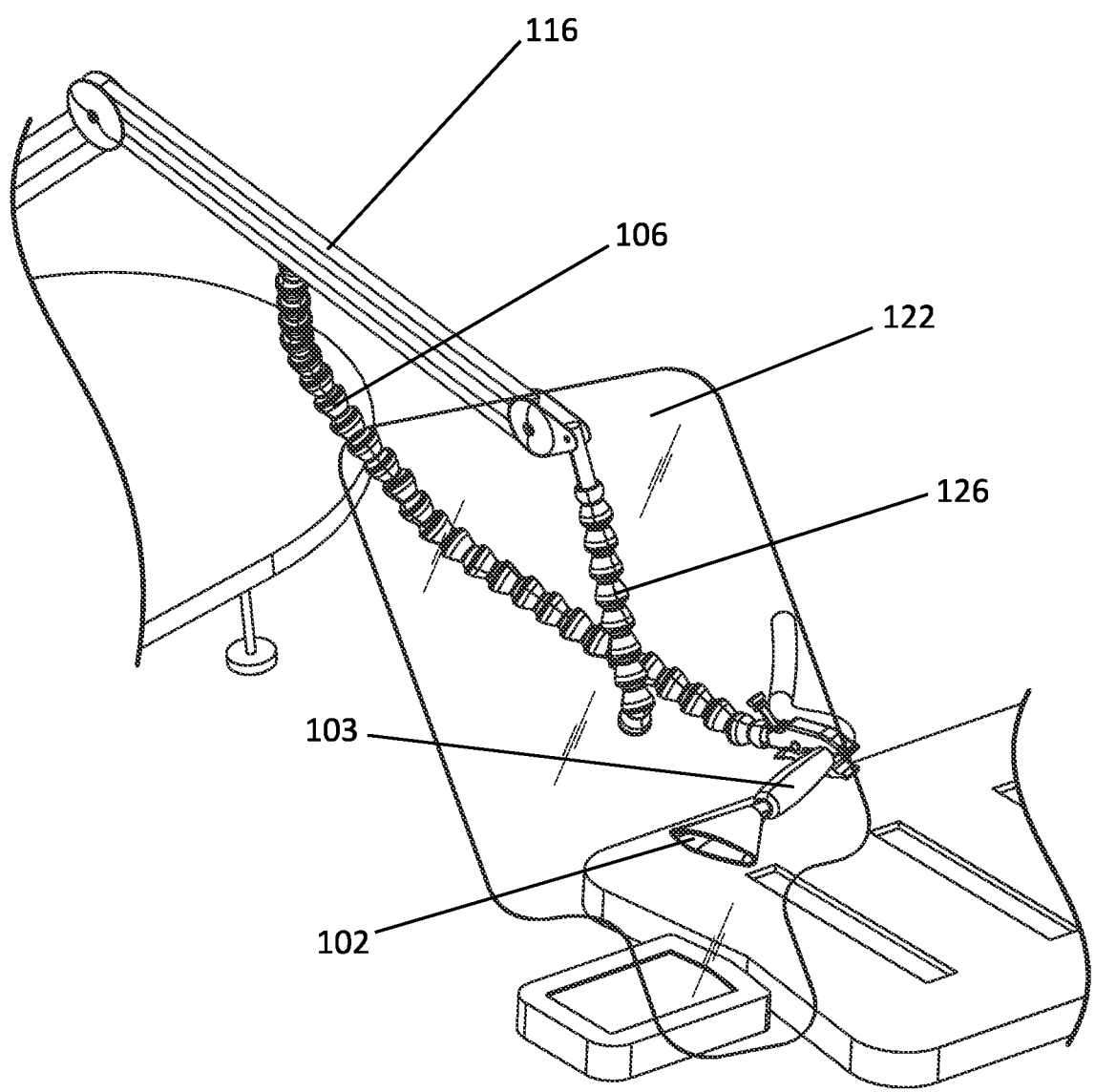
FIG. 4 is a perspective view of a dental aerosol protection system according to certain example embodiments.
Figure 5:
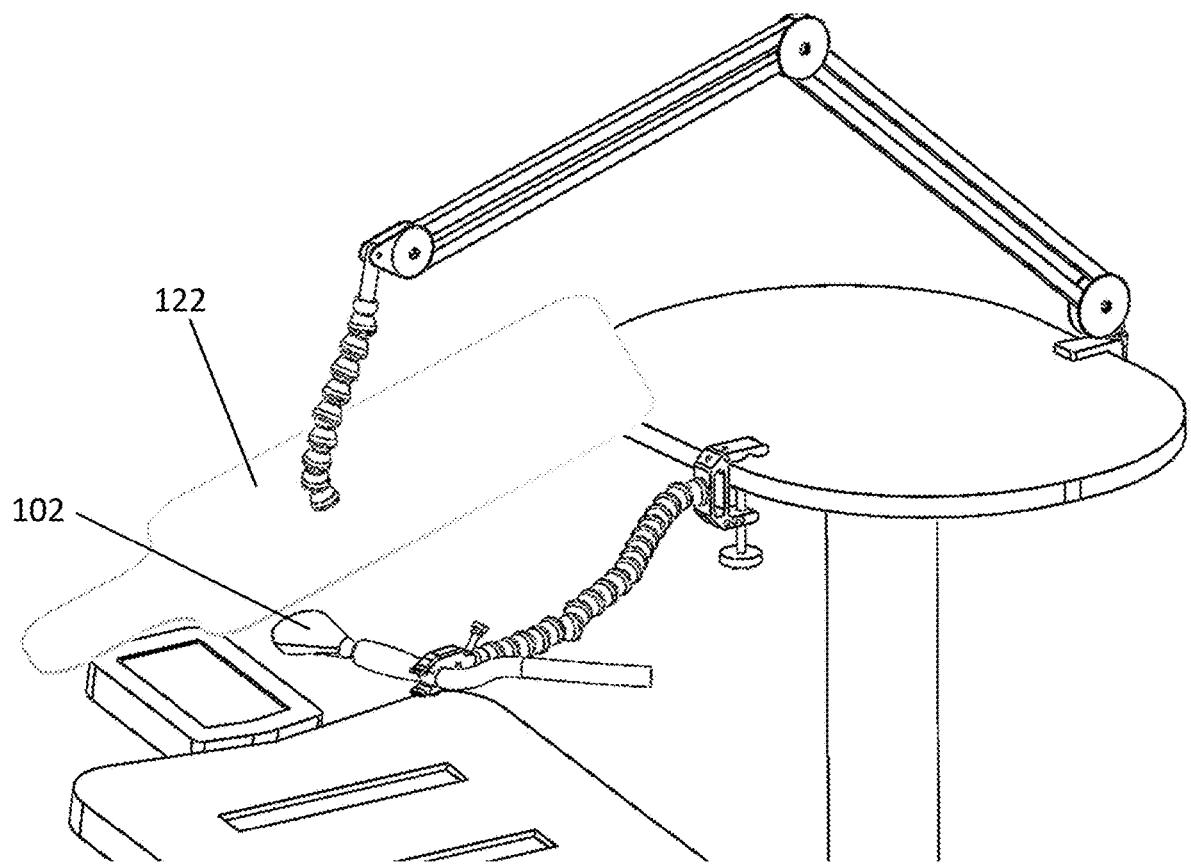
FIG. 5 is a perspective view of a dental aerosol protection system according to certain example embodiments.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

In the following descriptions, the present invention will be explained with reference to various example embodiments; nevertheless, these embodiments are not intended to limit the present invention to any specific example, environment, application, or particular implementation described herein. Therefore, descriptions of these example embodiments are only provided for purpose of illustration rather than to limit the present invention. The various features or aspects discussed herein can also be combined in additional combinations and embodiments, whether or not explicitly discussed herein, without departing from the scope of the invention.

Referring generally to FIGS. 1-9, the dental aerosol protection system 100 comprises an aerosol collection funnel 102 configured to be placed near the mouth of the patient to provide maximum suction of aerosols while not interfering with the dental practitioner's work. A proximal end (opposite the distal collection end) of the aerosol collection funnel 102 is configured to fit into the fitting of the distal end of a standardized high-vacuum evacuator (HVE) conduit 104 that is widely used in US dental clinics. The aerosol collection funnel 102 is also sized and shaped such that it fits into a SciCan Statim sterilizer (or similar sterilizer device) for sterilization between patients if desired.

The aerosol collection funnel 102 can be formed of a rigid plastic material or of a metal (e.g. stainless steel) or of a composite material. A combination of such materials can also be employed. The aerosol collection funnel 102 can be 3D-printed or molded in certain embodiments.

The aerosol collection funnel 102 disposed within the distal end fitting 103 of the HVE conduit 104 is held in the desired position and orientation by a fully adjustable arm 106. The arm 106 allows the dental practitioner to accurately position the aerosol collection funnel 102 adjacent to the mouth of the patient while minimizing any interference with the dental procedure. The arm 106 can then be easily re-positioned as the patient's recline angle is adjusted. Moreover, the arm easily accommodates any patient side when seated in the dental chair 101.

The proximal end 108 of the adjustable arm 106 is secured to a nearby table 110 or other stable structure with a clamp 112. The adjustable arm 106 extends distally from the clamp 112 and terminates in a distal clamp 114. The jaws of the distal clamp 114 are adjustable so that a portion of the HVE conduit 104 or its fitting can be secured by the distal clamp 114. The adjustable arm 106 can be a multi-adjustable snake-like arm that holds its set shape until a force is applied by the user sufficient to reposition or orient the arm 106.

The dental aerosol protection system 100 further comprises a self-balancing boom 116. The proximal end 118 of the boom 116 is secured to the nearby table 110. The boom 116 then extends distally and terminates in a floating distal end 120. The distal end 120 can be positioned above the patient's head.

Mounted to the distal end 120 of the boom 116 is a transparent shield 122. The shield can be formed as a polycarbonate sheet. The shield 122 provides a physical barrier between the patient and the dental practitioner(s) while allowing the practitioner(s) to see through it to provide care. Because the shield 122 is mounted to the distal end 120 of the boom 116, the shield can be adjusted to any placement and orientation desired by the dental practitioner(s). The boom 116 can be a self-balancing type. Thus, the shield 122 never has to touch the patient and can safely float above the patient's head. To allow the patient to be safely seated and unseated, the shield apparatus may be easily retracted with a one-handed operation.

Figure 6:
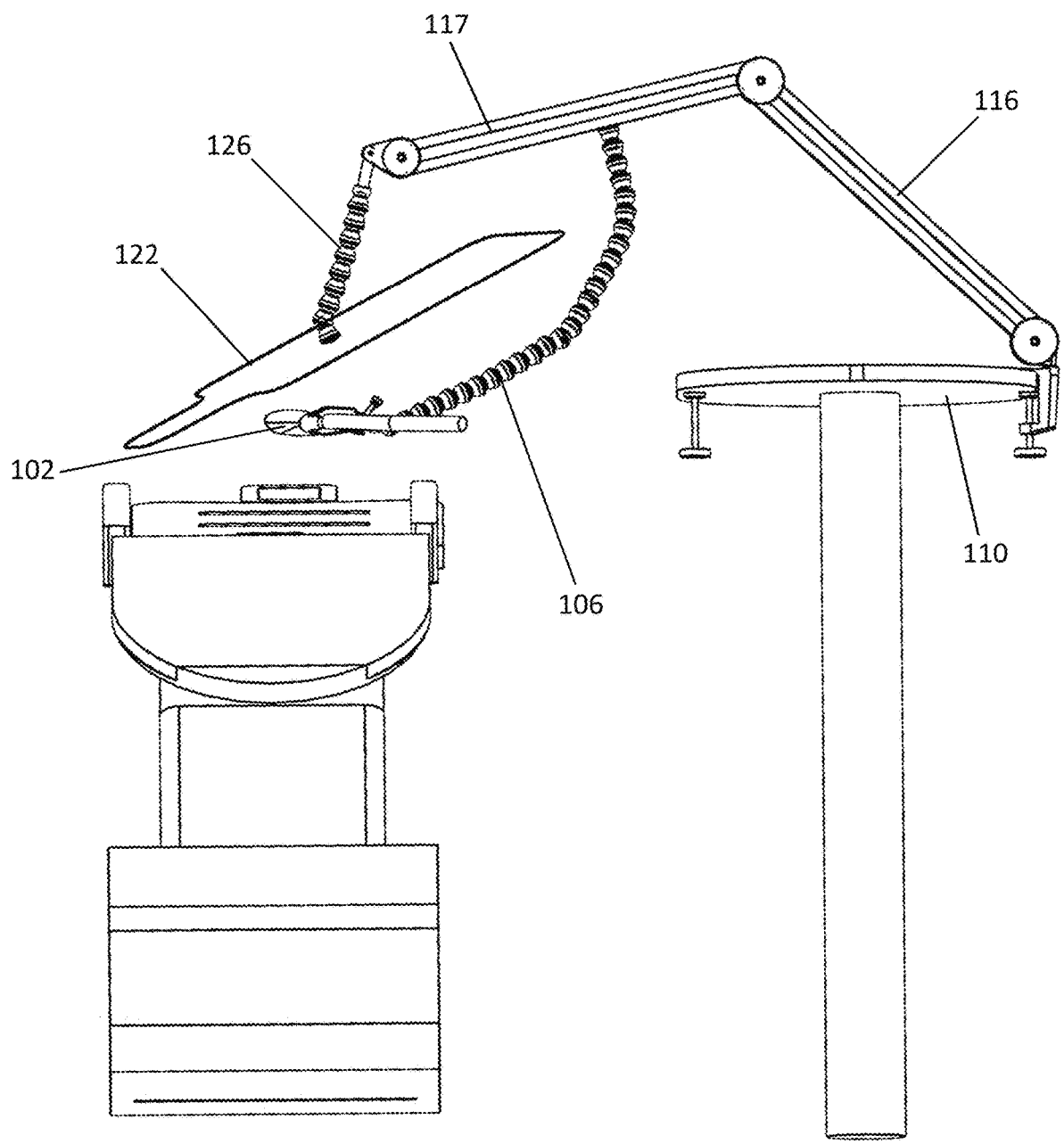
FIG. 6 is a front view of a dental aerosol protection system according to certain example embodiments.
Figure 7:
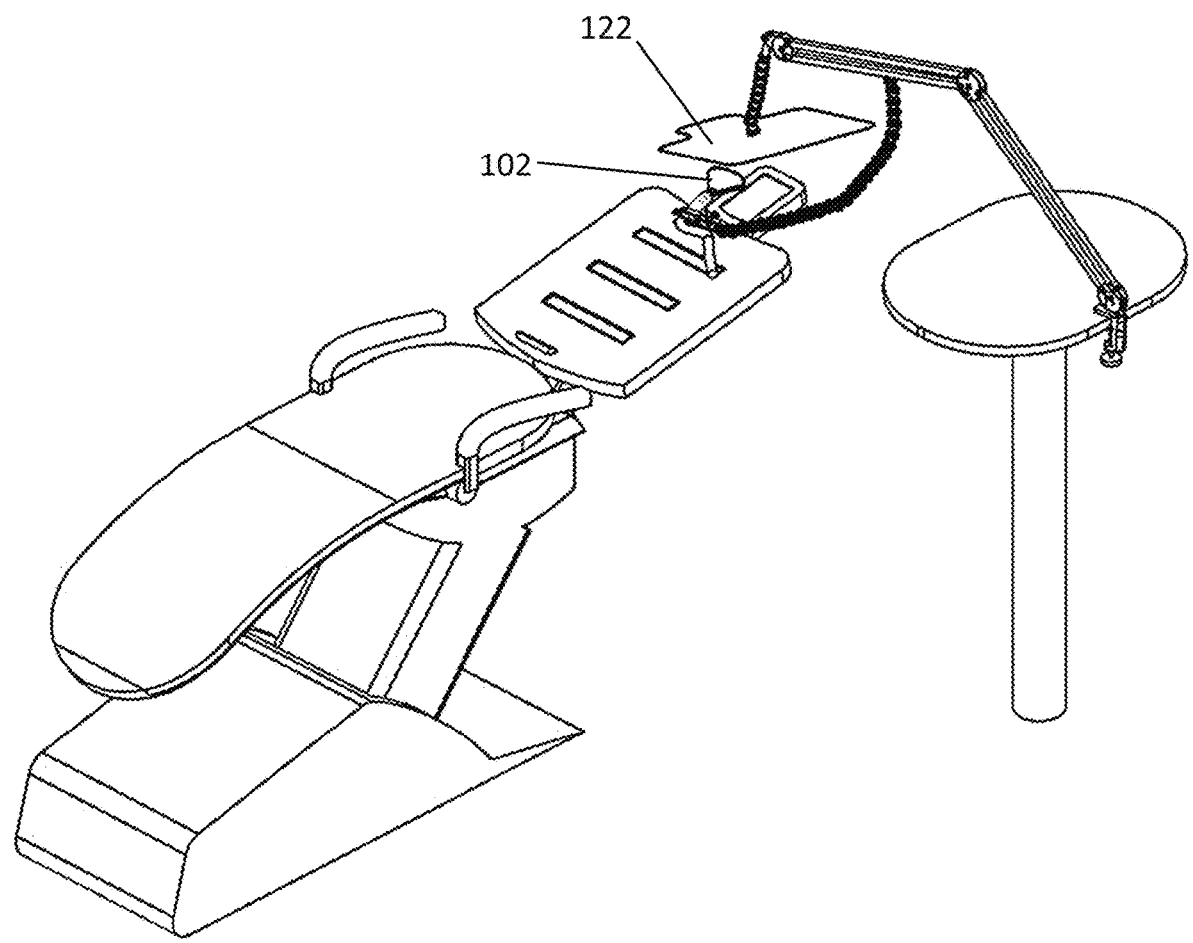
FIG. 7 is a perspective view of a dental aerosol protection system according to certain example embodiments.

FIGS. 6-7 show an alternative embodiment where the adjustable arm 106 is secured to the boom 116 instead of a table clamp. More specifically, the distal end of the adjustable arm 106 is secured to the distal-most span 117 of the boom 116.

The single shield variant of FIGS. 1-7 is adapted for use in dental hygiene settings where a single practitioner (e.g., a dental hygienist) is performing a cleaning. In this setting, only one shield 122 is typically needed, and the shield is relatively large in area for increased protection of the practitioner.

Figure 8:
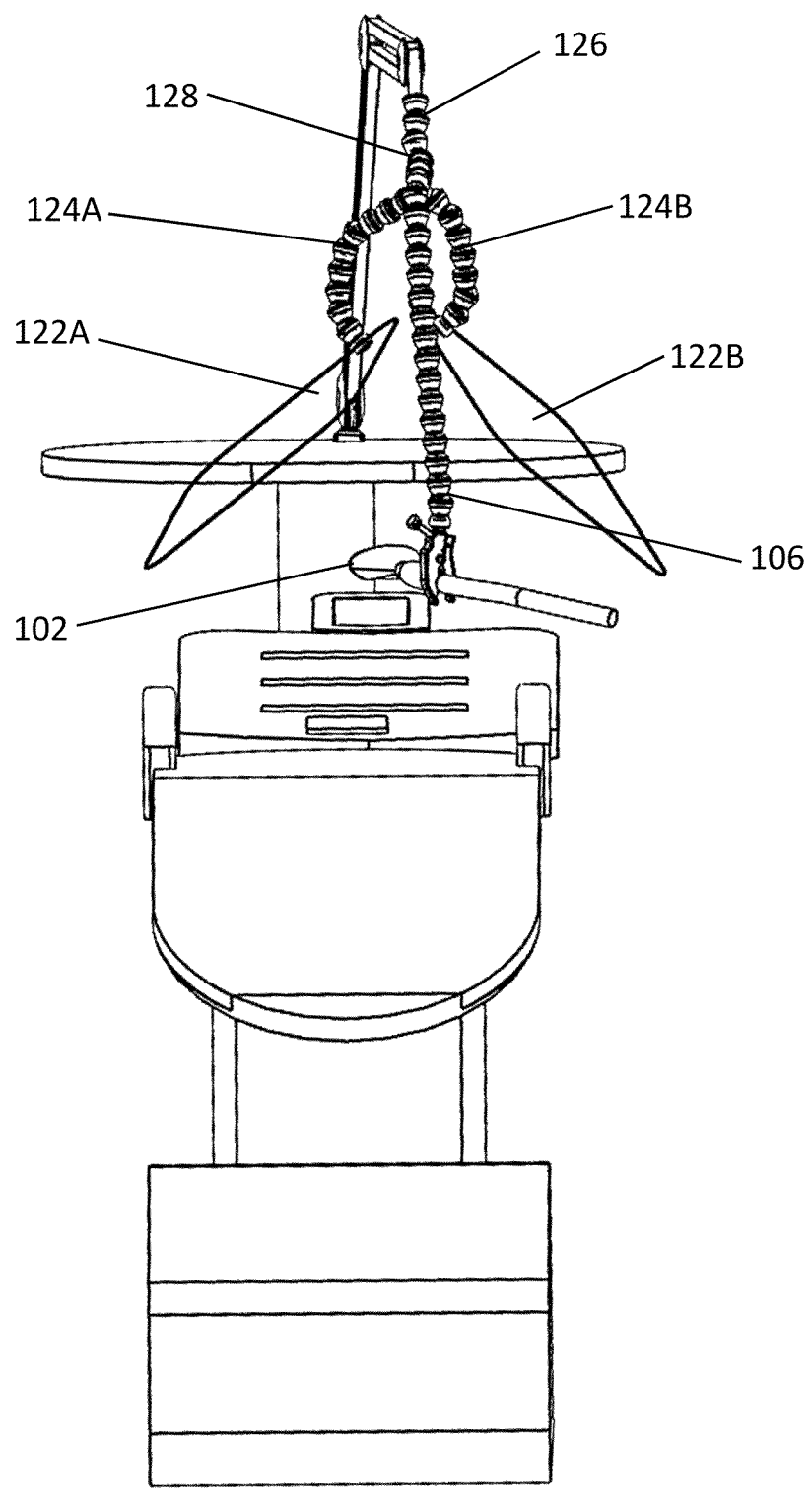
FIG. 8 is a front view of a dental aerosol protection system according to certain example embodiments.
Figure 9:
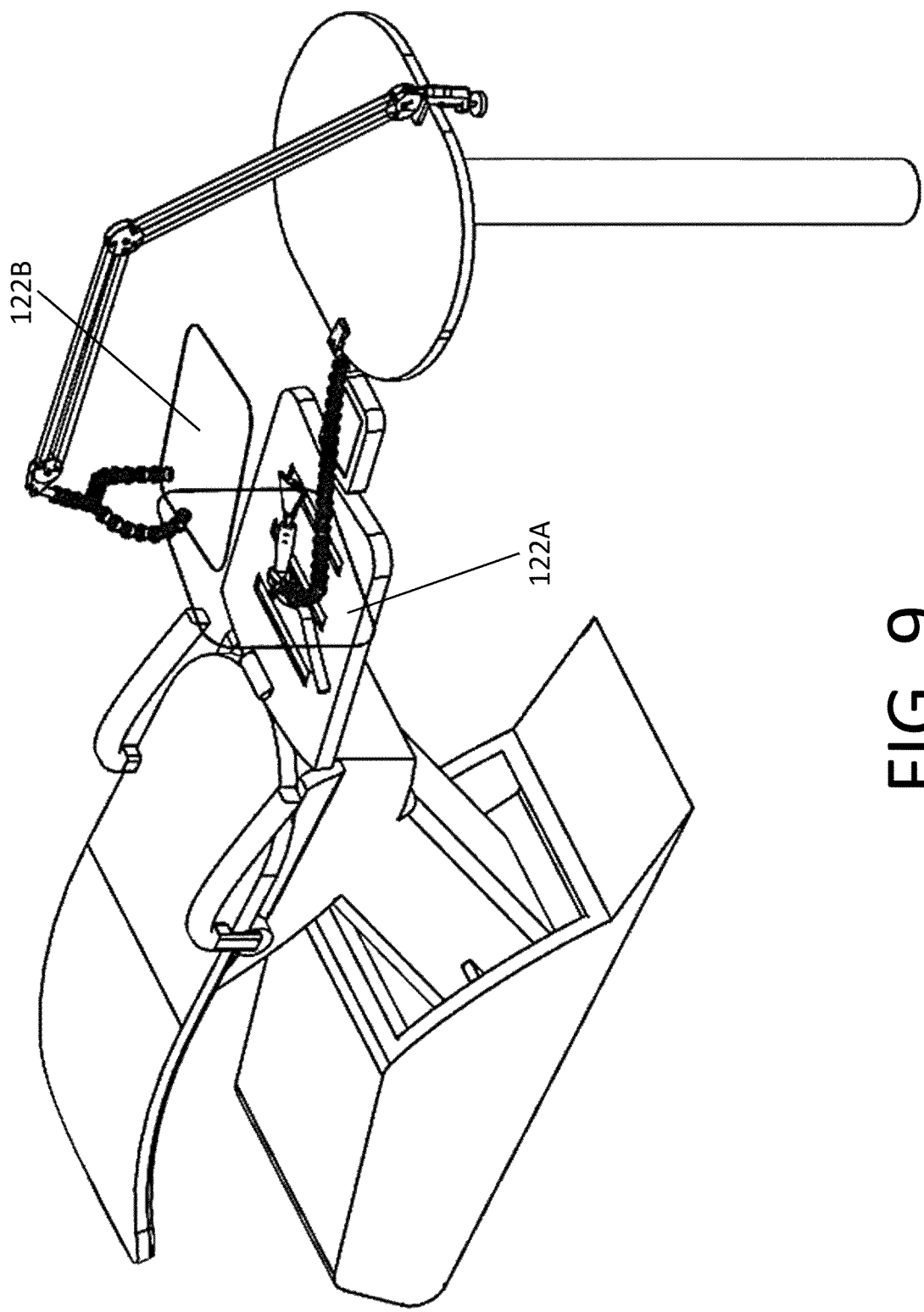
FIG. 9 is a perspective view of a dental aerosol protection system according to certain example embodiments.

A double shield variant of the system is shown in FIGS. 8-9. The dual shields 122A and 122B are adapted for use in standard dental settings where two practitioners (typically a dentist and an assistant) are performing a dental procedure together. In this setting, the two slightly smaller shields 122A and 122B (as compared to the single shield) protect each respective practitioner. The smaller areas of these shields 122A and 122B allow for greater independent adjustability of shield position without affecting the other shield as well as allowing the safe and effective usage and passing of instrumentation between dentist and assistant. Due to the wider range of dental procedures and the dynamic nature of a given procedure which may require physical repositioning of patient and practitioner seating positions, the smaller shields serve a protective function for a wider range of positions and are therefore better suited for use cases where two practitioners are treating a patient.

Each shield 122A and 122B in the double-shield embodiments is secured to the distal end of a leg 124A or 124B of a flexible shield support member 126. The legs 124A, 124B converge to define stem portion 128. The proximal end of the shield support member 126 is secured to the distal end 120 of the boom 116. The stem 128 and legs 124A, 124B can each be a snake-like flexible member. This allows the users to position the respective shields 122A and 122B in a desired position.

Figure 10:
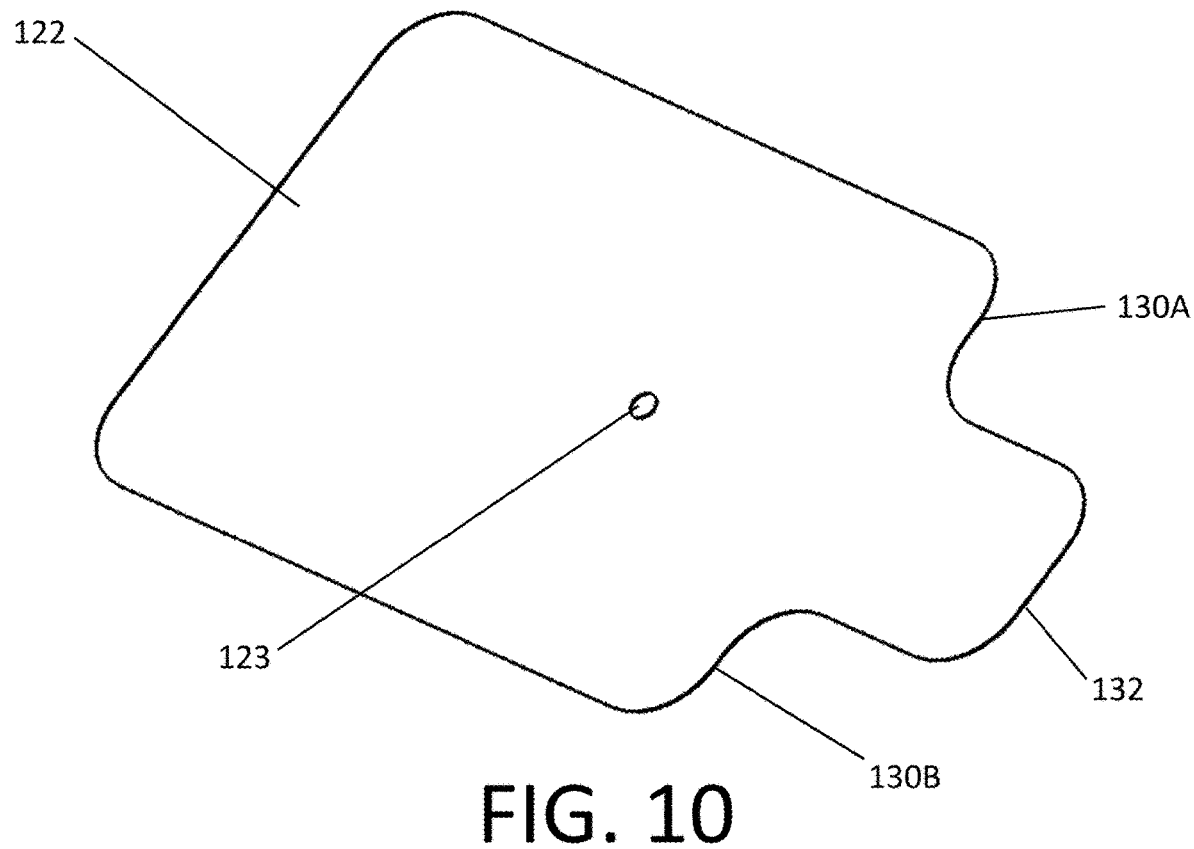
FIG. 10 is a perspective view of a shield for a dental aerosol protection system according to certain example embodiments.
Figure 11:
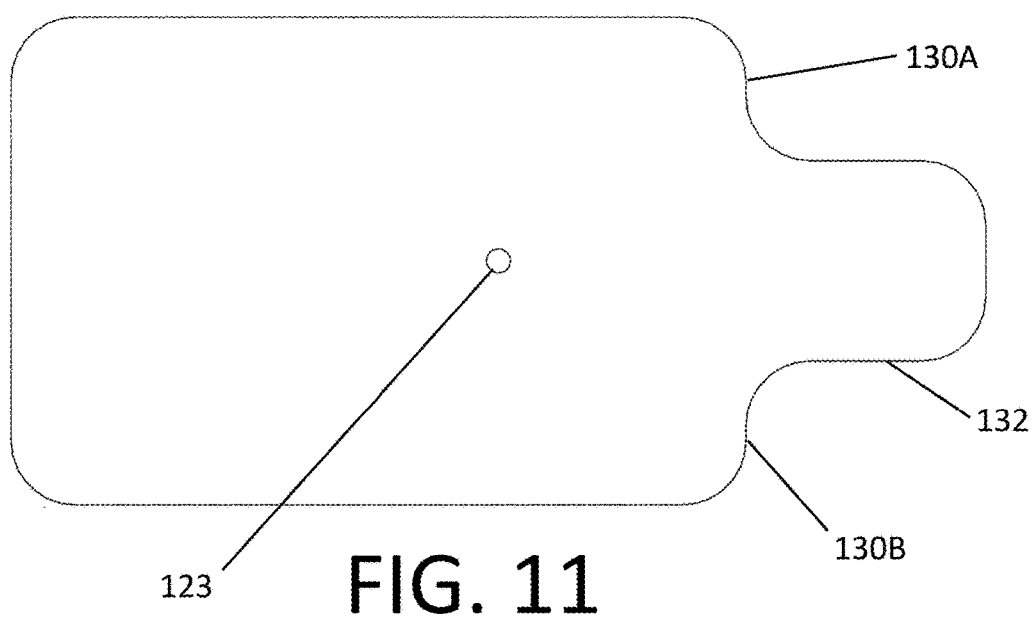
FIG. 11 is a top plan view of a shield for a dental aerosol protection system according to certain example embodiments.

Referring to FIGS. 10-11, the large single shield 122 is shown. This shield comprises a thin planar sheet of transparent material with an aperture 123 defined through the sheet at the sheet's approximate center. Three sides of the sheet define the sides of a rectangle with rounded corners. However, one of the minor-length sides is recessed inward to define shoulders 130A, 130B and a neck 132. The shoulder and neck features provide the dental practitioner with added clearance to perform procedures despite the relatively large size of the shied 122. In alternative embodiments, the shield 122 can be curved.

Figure 12:
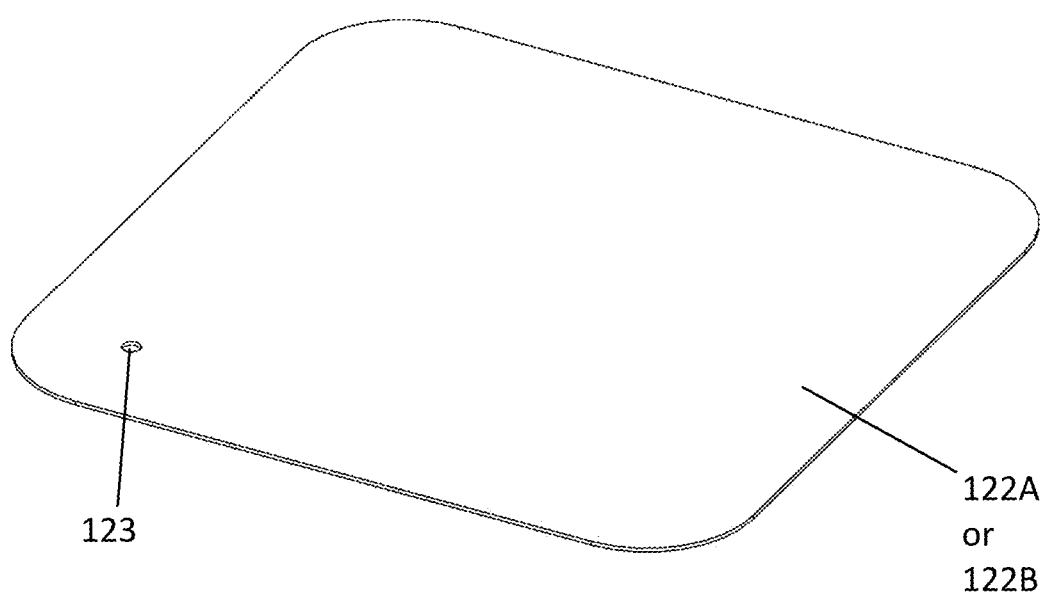
FIG. 12 is a perspective view of a shield for a dental aerosol protection system according to certain example embodiments.
Figure 13:
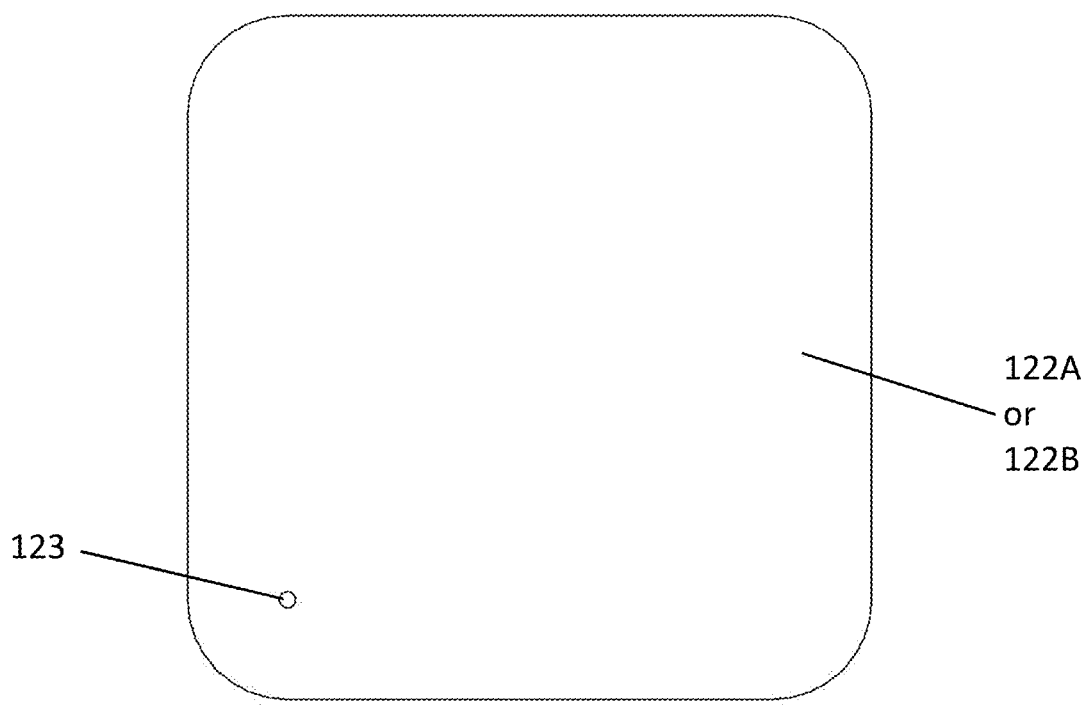
FIG. 13 is a top plan view of a shield for a dental aerosol protection system according to certain example embodiments.
Figure 14:
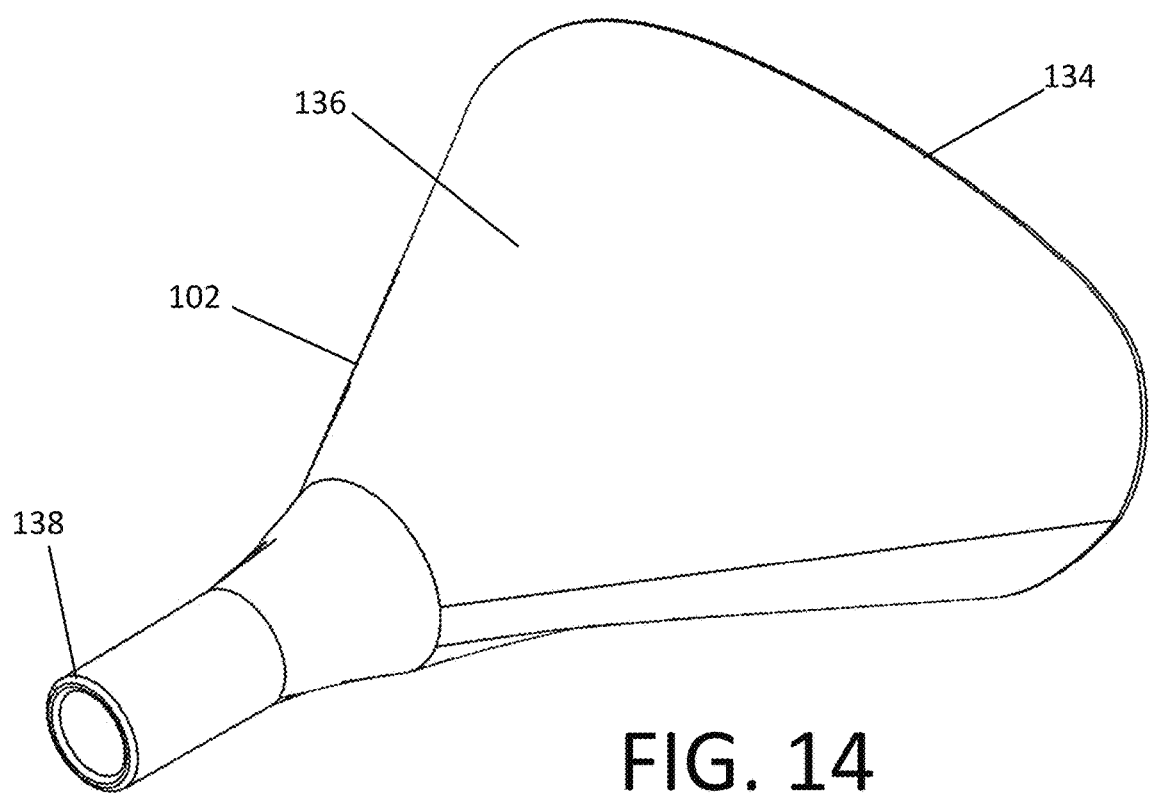
FIG. 14 is a perspective view of an aerosol collection nozzle for a dental aerosol protection system according to certain example embodiments.
Figure 15:
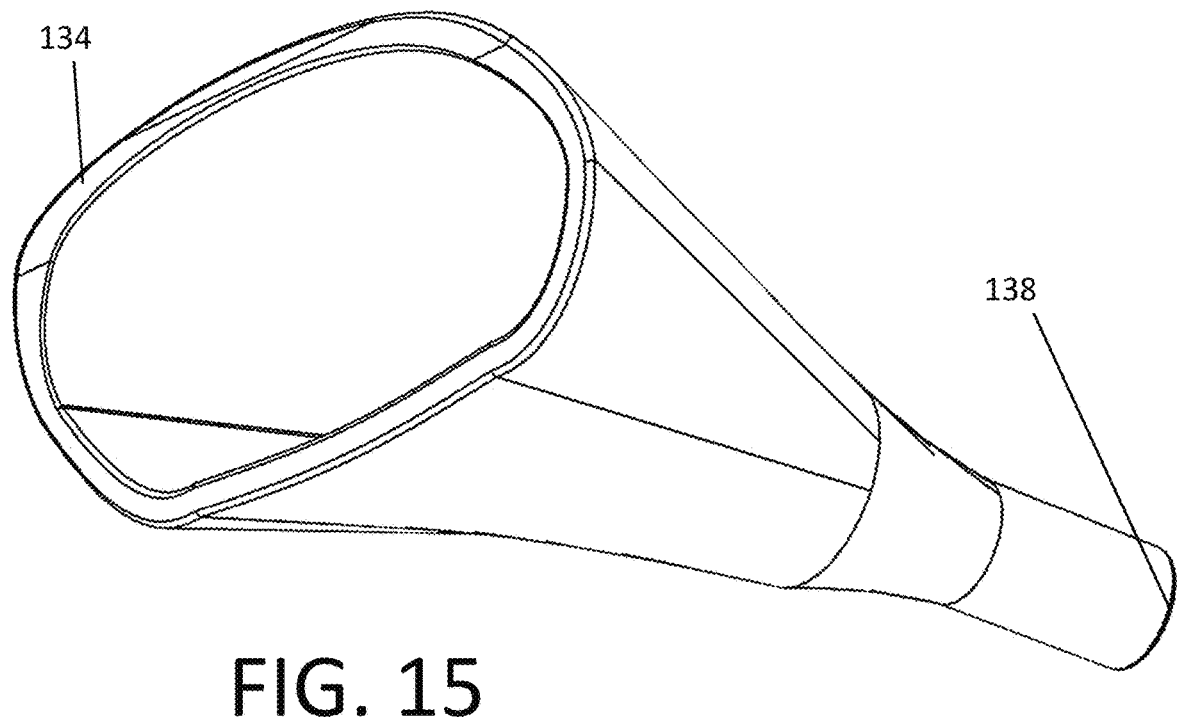
FIG. 15 is another perspective view of an aerosol collection funnel for a dental aerosol protection system according to certain example embodiments.

Referring to FIGS. 12-13, the shield 122A or 122B for use with double-shield embodiments is shown. This shield comprises a thin planar sheet of transparent material with an aperture 123 defined through the sheet at the sheet's center. The sheet defines a rectangle with rounded corners. In alternative embodiments, the shields 122A and/or 122B can be curved.

The shape of the shields 122, 122A and 122B can be varied to suit the user's particular needs, such as size and shape for clearance. For example, the shields can be circular, oval, ellipsoid, polygonal, complex or any combination thereof. The larger shield 122 can be used in double-shield embodiments with another similar shield or with the rectangular shield. The rectangular shield shape can also be used in the single shield embodiment.

An embodiment of the funnel 102 is shown in FIGS. 14-20. The distal end 134 defines the opening or collection end of the funnel. The body 136 of the funnel tapers from the distal end 134 towards the proximal end 138. The opposing proximal end defines a tubular section 140 sized and shaped to fit into the fitting of the distal end of a standardized HVE conduit used in most US dental clinics. An aperture extends longitudinally through the funnel 102 from the proximal to the distal ends. Thus, suction provided by the HVE conduit will allow the funnel to collect aerosols from the air adjacent to the distal end 134.

The shape of the distal end 134 has a flattened cone shape such that the horizontal dimension of the opening is greater than the vertical dimension of the opening. This shape approximates the opening of the patient's mouth, which is typically greater in the horizontal direction than in the vertical direction.

Figure 16:
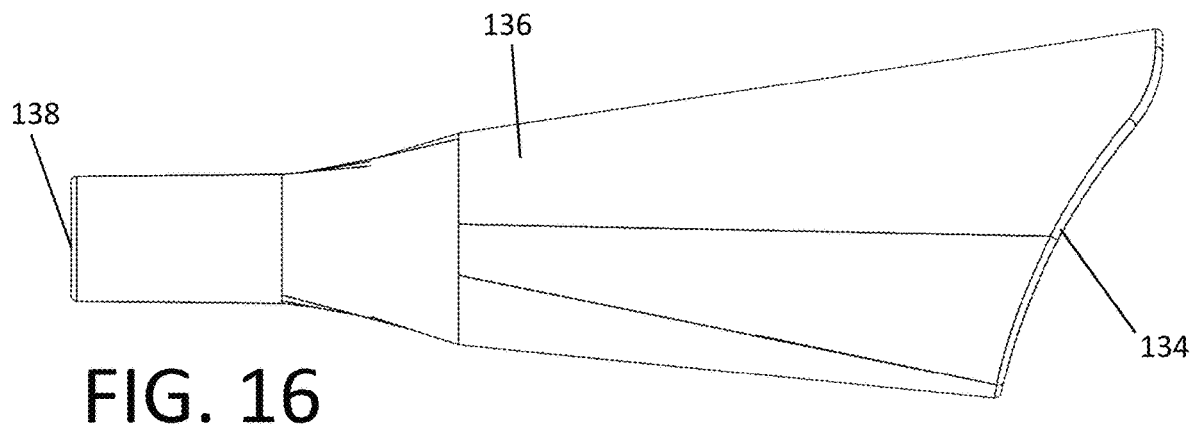
FIG. 16 is a side view of an aerosol collection funnel for a dental aerosol protection system according to certain example embodiments.
Figure 17:
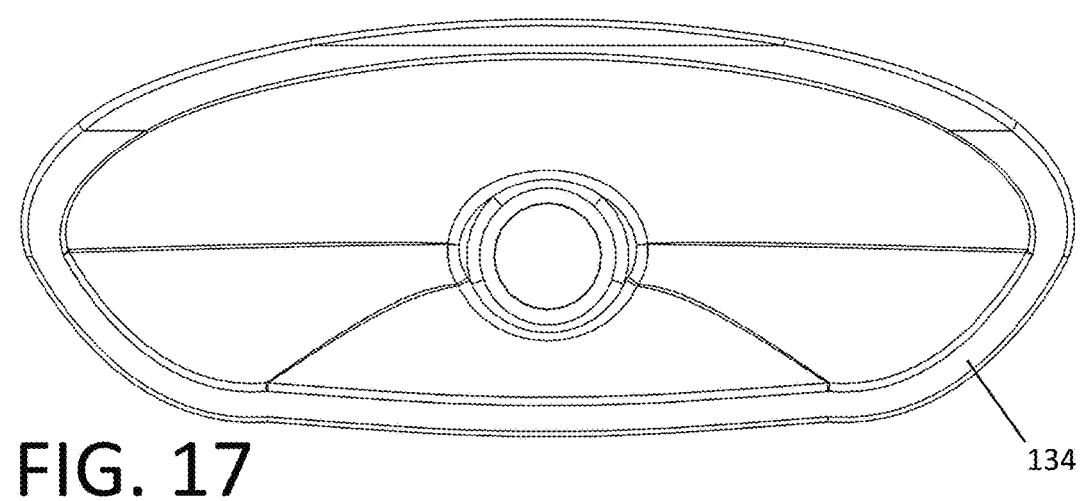
FIG. 17 is a front view of an aerosol collection funnel for a dental aerosol protection system according to certain example embodiments.
Figure 18:
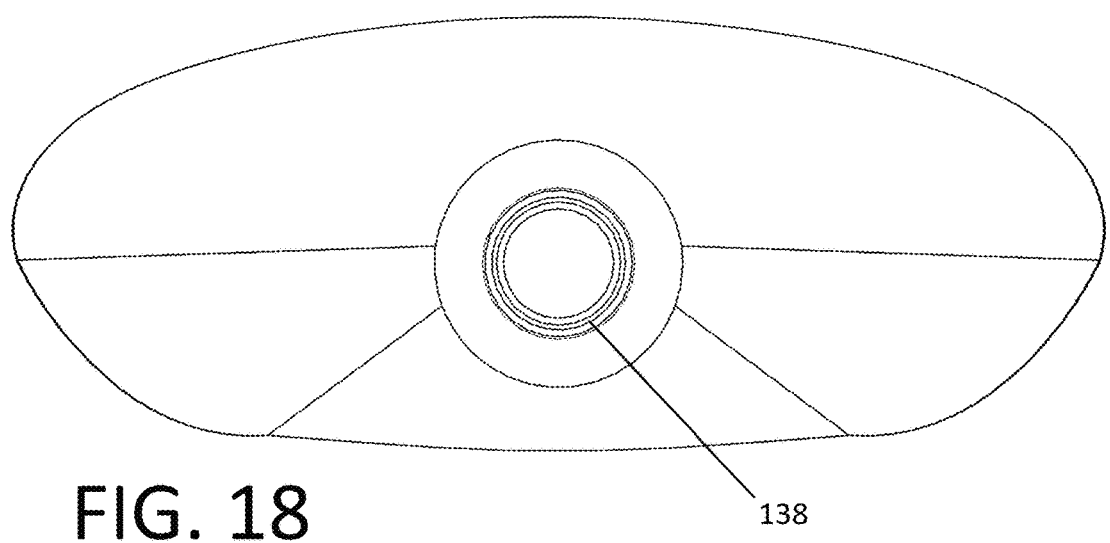
FIG. 18 is a rear view of an aerosol collection funnel for a dental aerosol protection system according to certain example embodiments.
Figure 19:
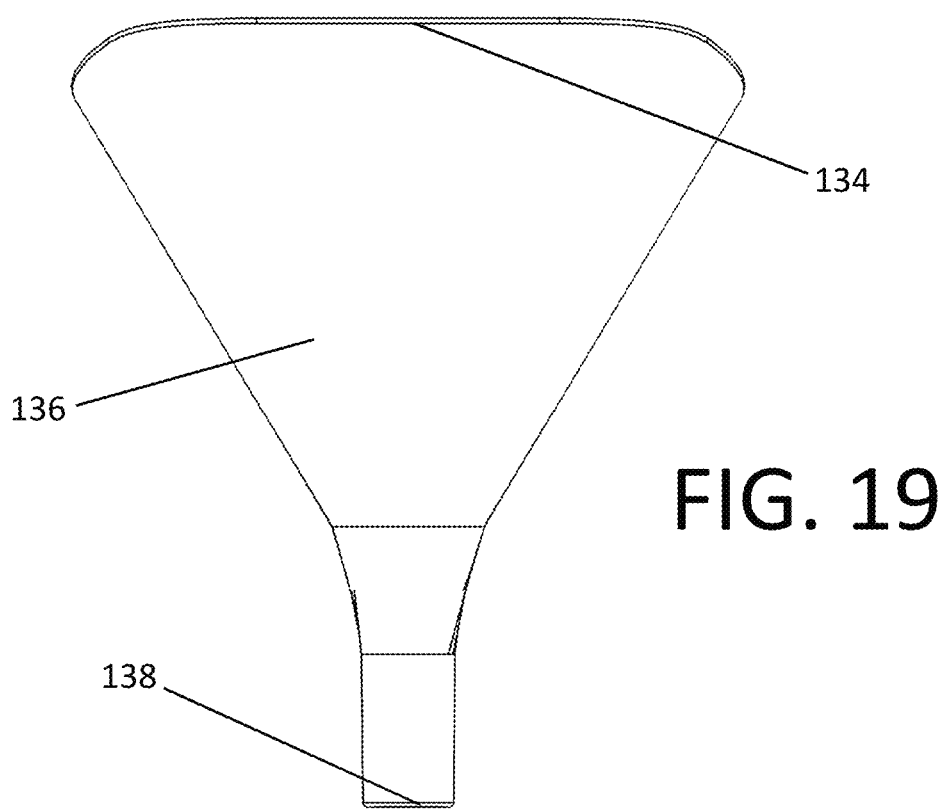
FIG. 19 is a top view of an aerosol collection funnel for a dental aerosol protection system according to certain example embodiments.
Figure 20:
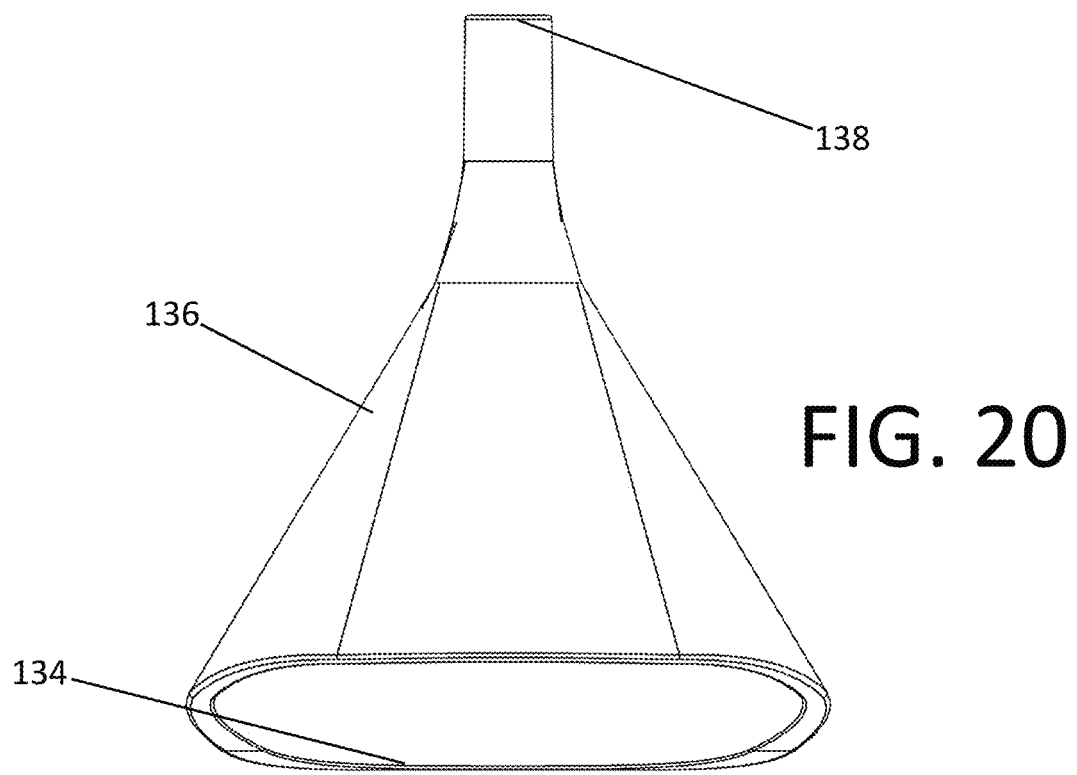
FIG. 20 is a bottom view of an aerosol collection funnel for a dental aerosol protection system according to certain example embodiments.

Also, as can be seen particularly in FIGS. 16 and 20, the opening at the distal end 134 is not in the vertical plane. Instead, the opening tapers inward towards the bottom surface such that the longitudinal length of the bottom surface is less than the longitudinal length of the top surface. This configuration creates a relatively larger opening area as compared to an opening that would be defined in side view at a right angle to the top and bottom surfaces. Moreover, the depicted shape functions to catch aerosols before they disburse upward from the patient's mouth. The depicted shape also allows the practitioner to position the funnel 102 coming from a lower angle, rather than directly perpendicular to the patient's mouth which would create a blocking obstacle to the practitioner.

Due to independent adjustability of the funnel 106 and shield(s) 122, the dental aerosol protection system 100 provides the dental practitioner(s) with the ability to position the shield(s) 122 and funnel 106 in the best position possible throughout a procedure without compromising aerosol suction. In contrast, conventional solutions provide shield adjustability at the expense of aerosol suction (as working space is made under the shield, vacuum suction is exponentially decreased).

The dental aerosol protection system 100 also can provide protection to two practitioners treating a given patient at the same time, unlike other systems which provide a single shield which may only protect one of the practitioners during treatment. The dental aerosol protection system 100 also provides increased protection for a single practitioner treating a patient.

The dental aerosol protection system advantageously utilizes existing high-volume evacuation (HVE) attachments found in all dental operatories. This eliminates the need for invasive and costly installation of standalone vacuum systems. The shield is designed for quick and non-invasive installation. Other solutions require invasive installations into the dental operatory and clinic as a whole.

In use, the dental practitioner inserts the funnel 102 into the fitting of the HVE conduit 104 and then secures the conduit 104 with the clamp 114 of the adjustable arm. The opposing end is either secured to a nearby stable object such as a table to an adjustable boom. One or more protective shields 122 are adjustably attached to the boom. The dental practitioner moves the shield into a position between the patient's face and the practitioner's face. The dental practitioner also moves the funnel so that the distal end thereof is located adjacent to the patient's mouth. Suction is activated for the HVE system and the dental procedure is performed. The components of the system 100 can be disinfected using conventional techniques prior to the next patient or components thereof can be swapped for previously sanitized components so the unsanitary components can be sanitized.

While the invention has been described in connection with what is presently considered to be the most practical and preferred example embodiments, it will be apparent to those of ordinary skill in the art that the invention is not to be limited to the disclosed example embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. A dental aerosol protection system, comprising:
an aerosol collection funnel, comprising a distal collection end and a proximal attachment end, wherein the proximal attachment end is configured to fit into a fitting of a high-vacuum evacuator (HVE) conduit, and wherein an aperture extends longitudinally through the funnel from the proximal attachment end to the distal collection end; and wherein the distal collection end defines an opening having a cross-sectional area that is greater than a diameter of the proximal attachment end; and
a shield comprising a transparent portion,
wherein the aerosol collection funnel is positionable with respect to a mouth of a patient via an adjustable arm operably coupled to the aerosol collection funnel or the fitting of the HVE conduit, and
wherein the shield is positional with respect to the mouth of the patient via a boom coupled to an aperture defined through the shield.

2. The dental aerosol protection system of claim 1, wherein the boom is a self-balancing boom and wherein a first end of the boom is secured to a rigid structure adjacent to the patient and the opposing second end is coupled to the shield.

3. The dental aerosol protection system of claim 1, wherein a first end of the adjustable arm is secured to a rigid structure adjacent to the patient and the opposing second end comprises a clamp that can secure the aerosol collection funnel or the fitting of the HVE conduit to the adjustable arm.

4. The dental aerosol protection system of claim 1, wherein a first end of the adjustable arm is secured to the boom and the opposing second end comprises a clamp that can secure the aerosol collection funnel or the fitting of the HVE conduit to the adjustable arm.

5. The dental aerosol protection system of claim 1, wherein the adjustable arm is operably coupled to the aerosol collection funnel or the fitting of the HVE conduit via a clamp.

6. The dental aerosol protection system of claim 1, wherein the aerosol collection funnel tapers from the distal collection end towards the proximal attachment end.

7. The dental aerosol protection system of claim 1, wherein the distal collection end of the aerosol collection funnel defines a flattened cone shape such that a horizontal dimension of an opening in the distal collection end is greater than a vertical dimension of the opening.

8. The dental aerosol protection system of claim 7, wherein the opening tapers inward from a top surface of the aerosol collection funnel to a bottom surface of the aerosol collection funnel.

9. The dental aerosol protection system of claim 1, further comprising a second shield, the second shield positional with respect to the mouth of the patient via the boom coupled to an aperture defined through the shield.

10. The dental aerosol protection system of claim 1, wherein the boom is coupled to the aperture defined through the shield via a flexible shield support member.

11. The dental aerosol protection system of claim 1, wherein the shield is a transparent sheet shaped as a rectangle with rounded corners.

12. The dental aerosol protection system of claim 1, wherein the shield is a transparent sheet shaped as a rectangle with rounded corners.

13. The dental aerosol protection system of claim 1, wherein the shield is a transparent sheet that is shaped to define a pair of shoulders and a neck portion between the pair of shoulders.

14. The dental aerosol protection system of claim 1, wherein the shield is a planar transparent sheet.

15. A method of protecting dental practitioners from aerosols emanating from a patient's mouth, the method comprising:
inserting a first end of an aerosol collection funnel into a fitting of an HVE conduit;
positioning a second end of the aerosol collection funnel adjacent to the patient's mouth;
securing a first transparent shield to a boom; and
adjusting a position of the first transparent shield independent of the position of the aerosol collection funnel so that the first transparent shield lies between the patient's mouth and a dental practitioner while the dental practitioner is performing a dental procedure on the patient.

16. The method of claim 15, further comprising:
securing a second transparent shield to the boom; and
adjusting a position of the second transparent shield independent of the position of the aerosol collection funnel so that the second transparent shield lies between the patient's mouth and a second dental practitioner while the second dental practitioner is performing the dental procedure on the patient.

17. The method of claim 15, further comprising clamping the aerosol collection funnel to an adjustable arm.

18. The method of claim 17, further comprising securing an end of the adjustable arm opposite the clamped aerosol collection funnel to either the boom or a rigid structure within a dental operatory where the dental practitioner is performing the dental procedure on the patient.

19. The method of claim 15, wherein the step of securing the first transparent shield to the boom comprises fastening the first transparent shield to a first end of a flexible shield support member via an aperture defined through the first transparent shield and fastening a second end of the flexible shield support member to the boom.

20. The method of claim 15, further comprising securing the boom to a rigid structure within a dental operatory where the dental practitioner is performing the dental procedure on the patient.

\* \* \* \* \*